(12) United States Patent
Baviera et al.

(10) Patent No.: US 8,450,694 B2
(45) Date of Patent: May 28, 2013

(54) STAND-ALONE MINI GAMMA CAMERA INCLUDING A LOCALIZATION SYSTEM FOR INTRASURGICAL USE

(75) Inventors: Jose Maria Benlloch Baviera, Valencia (ES); Filomeno Sanchez Martinez, Valencia (ES); Christoph Lerche, Valencia (ES); Noriel Pavon Hernandez, Valencia (ES); Jesus Modia Leiva, Valencia (ES)

(73) Assignees: Consejo Superior de Investigaciones Cientificas, Madrid (ES); Universidad de Valencia, Valencia (ES)

( * ) Notice: Subject to any disclaimer, the term of this patent is extended or adjusted under 35 U.S.C. 154(b) by 797 days.

(21) Appl. No.: 12/159,307

(22) PCT Filed: Dec. 22, 2006
(Under 37 CFR 1.47)

(86) PCT No.: PCT/ES2006/070200
§ 371 (c)(1),
(2), (4) Date: Apr. 27, 2009

(87) PCT Pub. No.: WO2007/074201
PCT Pub. Date: Jul. 5, 2007

(65) Prior Publication Data
US 2010/0025587 A1 Feb. 4, 2010

(30) Foreign Application Priority Data
Dec. 26, 2005 (ES) .................................. 200503198

(51) Int. Cl.
*A61B 19/00* (2006.01)
*G01T 1/29* (2006.01)

(52) U.S. Cl.
USPC ............... 250/363.04; 250/370.11; 600/407

(58) Field of Classification Search
USPC ............. 250/361 R, 370.09, 370.11; 600/407
See application file for complete search history.

(56) References Cited

U.S. PATENT DOCUMENTS

| 3,011,057 | A | | 11/1961 | Anger |
| 4,929,835 | A | * | 5/1990 | Yamashita et al. ............ 250/367 |
| 5,429,135 | A | * | 7/1995 | Hawman et al. .............. 600/436 |
| 5,876,630 | A | * | 3/1999 | Vinograd et al. ...... 252/301.4 H |

(Continued)

OTHER PUBLICATIONS

Norbeck et al (1995). "Preparation of CsI(TI) for Charged Particle Detection." Nucl. Inst. Methd. Phys. Research A (360): p. 642-644.*

(Continued)

*Primary Examiner* — Casey Bryant
(74) *Attorney, Agent, or Firm* — Leason Ellis LLP (57) ABSTRACT

The invention relates to a portable mini gamma camera for intrasurgical use. The inventive camera is based on scintillation crystals and comprises a stand-alone device, i.e. all of the necessary systems have been integrated next to the sensor head and no other system is required. The camera can be hot-swapped to any computer using different types of interface, such as to meet medical grade specifications. The camera can be self-powered, can save energy and enables software and firmware to be updated from the Internet and images to be formed in real time. Any gamma ray detector based on continuous scintillation crystals can be provided with a system for focusing the scintillation light emitted by the gamma ray in order to improve spatial resolution. The invention also relates to novel methods for locating radiation-emitting objects and for measuring physical variables, based on radioactive and laser emission pointers.

21 Claims, 6 Drawing Sheets

U.S. PATENT DOCUMENTS

| | | | |
|---|---|---|---|
| 5,961,458 A * | 10/1999 | Carroll | 600/436 |
| 6,232,605 B1 | 5/2001 | Soluri et al. | |
| 6,242,744 B1 * | 6/2001 | Soluri et al. | 250/363.1 |
| 6,271,525 B1 * | 8/2001 | Majewski et al. | 250/367 |
| 6,723,988 B1 * | 4/2004 | Wainer | 250/336.1 |
| 6,781,134 B1 * | 8/2004 | Murray et al. | 250/370.13 |
| 7,142,638 B2 * | 11/2006 | Polichar et al. | 378/98.8 |
| 7,220,961 B2 * | 5/2007 | Chapman | 250/252.1 |
| 7,649,178 B2 * | 1/2010 | Petrillo et al. | 250/370.09 |
| 2002/0102395 A1 * | 8/2002 | Duclos | 428/297.4 |
| 2003/0081716 A1 * | 5/2003 | Tumer | 378/19 |
| 2004/0075058 A1 * | 4/2004 | Blevis et al. | 250/370.09 |
| 2004/0262528 A1 | 12/2004 | Zaikin et al. | |
| 2006/0086311 A1 * | 4/2006 | Zagumennyi et al. | 117/13 |
| 2007/0015987 A1 * | 1/2007 | Benlloch Baviera et al. | 600/407 |
| 2007/0152161 A1 * | 7/2007 | Olcott et al. | 250/363.07 |

OTHER PUBLICATIONS

Sanchez, F. et al., Design and tests of a portable mini gamma camera, Med. Phys. vol. 31, No. 6, pp. 1384-1397, 2004.

Porras, E. et al., Portable mini gamma camera for medical applications, Nuclear Instruments & Methods in Physics Research, vol. 486, pp. 186-190, 2002.

Anger, H. O., Scintillation Camera, The Review of Scientific Instruments, vol. 29, No. 1, pp. 27-33, 1958.

Gimenez, M. et al., Medium field of view multiflat panel-based portable gamma camera, Nuclear Instruments & Methods in Physics Research, vol. 525, pp. 298-302, 2004.

Fernandez, M.M. et al., A flat-panel-based mini gamma camera for lymph nodes studies, Nuclear Instruments & Methods in Physics Research, vol. 527, pp. 92-96, 2004.

NEMA Standards Publication NU Jan. 1994, Performance Measurements of Scintillation Cameras, National Electrical Manufacturers Association, 1994.

McElroy, D.P. et al., The Use of Retro-Reflective Tape for Improving Spatial Resolution of Scintillation Detectors, IEE Transaction of Nuclear Science, vol. 49, No. 1, pp. 165-171, 2002.

* cited by examiner

STAND-ALONE MINI GAMMA CAMERA INCLUDING A LOCALIZATION SYSTEM FOR INTRASURGICAL USE

This application is a U.S. national phase application under 35 U.S.C. §371 of International Patent Application No. PCT/ES2006/070200 filed Dec. 22, 2006, which claims the benefit of priority to Spanish Patent Application No. P200503198 filed Dec. 26, 2005, the disclosures of all of which are hereby incorporated by reference in their entireties. The International Application was published in Spanish on Jul. 5, 2007 as WO 2007/074201.

FIELD OF THE INVENTION

The present invention belongs to the field of Medical Nuclear Physics and radioguided surgery. It is a device that makes it possible to produce in vivo images of small human and animal organs using radioisotopes that are traditionally used in nuclear medicine, with a high resolution and in real time. The device is designed for functional studies and detection and/or precise localisation of cancer in organs such as the thyroid gland, kidneys, prostate, breasts and lymph nodes. It is applicable to preliminary, intra-operative and postoperative diagnosis.

PRIOR ART

In the diagnostic procedures used in nuclear medicine, the patient is first given a radiopharmaceutical. A radiopharmaceutical is a chemical compound containing isotopes that emit radiation, usually gamma rays. Once said compound has been spread naturally throughout the patient's body, the latter is examined using a gamma ray detection camera, which provides information about the region of the organism where the radiopharmaceutical has accumulated.

Gamma cameras have been improved since they were first created in 1958 (H. O. Anger, Rev. Sci. Instrum. 29 (1958) 27), but they have traditionally consisted of large pieces of equipment, weighing hundreds of kilograms and they have been connected to bulky, complex electronic systems. This equipment is produced, distributed and installed by major transnational companies (GENERAL ELECTRIC, Siemens, etc.) in specific hospital premises.

The detection technology used by these cameras is mainly based on scintillation crystals and photomultiplier tubes (PMT) that are not position sensitive.

The first small gamma cameras, also called mini gamma cameras, came onto the market relatively recently, such as those produced by Anzai Medical, TeraRecon, Intra Medical Imaging, EuroMedical Imaging, and Gamma Medica Imaging. The objective of mini cameras is to cover part of the diagnosis where they can provide a much higher quality image than large cameras, in addition to the advantage of being less costly and often portable equipment. Meanwhile, new fields of application that are almost impossible for large equipment are being discovered for mini cameras, such as intra-operative use.

Some mini gamma cameras now use a new type of detection technology based on a Zinc-doped Cadmium Telluride semiconductor (CdZnTe), e.g. Anzai Medical and TeraRecon).

In the following paragraphs we will give a brief description of the patents covering mini gamma cameras that are related to the present invention.

US 2004/0262528, invented by R. Zaikin and M. Suzuki, relates to a gamma camera with a small field of view that comprises several modules. It uses a crystal array and photodiodes coupled to the crystals. Claim 22 refers to the use of pixelated CsI(TI) crystals. Claim 10 refers to the fact that the camera's high-voltage power supply is provided by an electronic card on the computer interface (a PCI card, if applicable). It can be observed that the PCI bus shares dozens of data lines and the power supply with the computer's motherboard and, furthermore, it is inside the computer, which means opening the CPU and inserting the PCI card with the computer switched off so that it is subsequently available to provide the camera with a high-voltage power supply, this not being the only power supply that it requires.

US2003/0081716 A1, invented by T. Tumer, relates to the invention of a hand-held, compact portable probe with an LCD display (connected by cable or radio). The technology used in this detector is based on semiconductors, and more specifically on CdZnTe. However, claim 19 refers to the fact that the detector material can also be selected from the following group: HPGe, BGO, CdWO4, CsF, NaI(TI), CsI(Na), CsI(TI), CdTe, CdZnTe, HgI2, GaAs, PbI2. However, it does not make any mention of whether it concerns continuous or pixelated crystals.

ES 2202846, invented by A. Soluri and R. Pañi, relates to a flat scintillation gamma camera with very high spatial resolution with a modular structure. The photomultipliers mentioned in the patent are of the position sensitive type with crossed wire anode readout.

ES 2206924, invented by A. Soluri, relates to a miniaturised camera measuring 30 mm×30 mm, with pixelated crystal and individual amplification and acquisition systems for each channel, which are external to the detector head. However, claim 13 refers to any position sensitive type photomultiplier.

WO 00/19238 (S. Majewski, A. Weisenberger, and R. Wojcik) claims all types of small scintigraphy equipment consisting of arrangements of position sensitive detectors. It also relates to equipment with a small detector head, but which requires standard modular electronic systems (e.g. CAMAC or NIM) to operate.

As can be seen, mini scintillation gamma cameras generally use one or more position sensitive photomultipliers to achieve small equipment. However, it is the head where the detector (the scintillation crystal together with the photomultiplier) is located that is reduced to make them more manageable than the large commercial cameras. For their operation both the large cameras and the aforementioned mini cameras require a set of electronic systems mounted in bulky standard racks, such as CAMAC or NIM, or the usual cards that are inserted into the computer. To put even the most advanced cameras or mini gamma cameras into operation it is currently necessary for the equipment to be supplied with the calculation or computer system with the electronics included, whether this be a card in a standard computer or a calculation system specifically designed for the camera.

Therefore, there are no stand-alone mini gamma cameras based on scintillation crystals, i.e. in which their detection, electronic and power supply system are integrated into a small single sensor head, without any active part outside the camera, such as PCI cards in the computer. Likewise, there are no mini gamma cameras that can be plugged in and unplugged without having to switch the computer off and in which all the necessary voltages for their operation, including high voltage, are generated inside the camera and not on a card or other device that is connected to the computer.

Most of said patents relate to pixelated crystals. Some make a minor mention of the possibility of using continuous crystals of a certain chemical composition. However, none of said patents explain how to overcome the serious edge and compression problems affecting the image that occur when the detection surface is small in relation to the width of the crystal, in the direction in which the gamma rays enter, as is the case, by definition, with mini gamma cameras.

Some of said patents use photodiodes but most use wire-based position sensitive photomultipliers. There are therefore no mini gamma cameras based on position sensitive photomultipliers based on pad type anodes and in particular on flat panel type anodes, which had not yet been invented when said patents were registered. The research group of the Institute of Corpuscular Physics (IFIC), formed by the inventors of the present invention, has also developed several prototypes of mini gamma cameras. The design and operational characteristics of these prototypes were described in several articles published in scientific publications. One of said prototypes used wire photomultipliers (different to the technology used herein) (Nucl. Instr. & Meth. A486 (2002)186-190, Med. Phys. 31, 6 (2004) 1384-1397). A first version of the prototype operated with cards inserted into the computer and the other could send the data via its USB 1.0 port.

Subsequently, two prototypes were developed based on flat panel photomultipliers (M. Giménez, et al., Nucl. Instr. & Meth. A525 (2004) 298-302; Nucl. Instr. & Meth. A527 (2004)92-96). One of them had a medium-sized field of view, and consisted of an arrangement of 4 PMTs; the other consisted of a single flat panel type PMT. Both had a rectangular prismatic metal casing and could send data via the USB 1.0 port. They had continuous crystals treated with paint on both sides of the crystal.

With all the IFIC's aforementioned prototypes and publications there is the problem that in practice the limited broadband (1.2 Mbps) of the USB port used (1.0) only makes it possible to reach a low rate of event acquisition (maximum 1100 counts per second) in relation to the normal rate used in nuclear medicine, even though the physical detector was capable of acquiring data at a greater speed. One object of the present invention is a mini gamma camera that can operate using the USB 1.1, USB 2.0 port and reach a broadband connection of up to 480 Mbp, allowing it to communicate up to 400 times faster, which means that it can acquire data at the high rates needed to achieve high sensitivity.

Moreover, all these prototypes developed by the IFIC presented the problem that they were not suitable for medical use, making their practical application in humans unviable for both diagnostic and intra-operative use. This is due to strict biocompatibility, electrical safety and electromagnetic compatibility conditions imposed by European and American regulations governing medical equipment.

Lastly, the painting technique used to treat the surfaces of the crystals used in the IFIC's prototypes and publications was practically unworkable, as there were many defects at the edges and there were inhomogeneities throughout the sensitive area, which gave the sensor systems thus created a very short useful life and caused losses of uniformity that were unacceptable according to medical standards.

There is no known mini gamma camera using any of the current technologies that has a standard computer as a calculation system and that can be plugged into and unplugged from the computer without interrupting its operation or switching it off, and which can start to be used immediately without adding any other intermediary electronic systems.

Likewise, there are no known cameras or mini gamma cameras that produce real time video gamma images, or still images in a few seconds, using the low doses of radiation permitted in nuclear medicine.

The difficulties found with the intra-surgical use of mini gamma cameras include viewing low-activity regions (such as lymph nodes) close to high-activity points (such as peritumoural injection sites). One solution that is commonly applied by nuclear physicians consists of establishing an anti-radiation screen ("material that is opaque" to gamma rays) between the tumour and the camera (normally a piece of lead). This makes it possible to eliminate the glare from the tumour so that the low-activity points can be seen, as the intensity of image is redistributed only between the low-activity values, which include lymph nodes that were previously invisible. It will be seen below how this idea can be extended for a different purpose by adding IT tools, making it possible to create a new method for the spatial localisation of observable regions of the scintigraphic image, which is precisely another of the difficulties to overcome.

As has just been mentioned in the previous paragraph, another of the problems presented by mini gamma cameras is that of locating objects that appear in the images that they capture in the patient's body, i.e. the correspondence between image and organism.

To partially solve this problem, doctors sometimes use a radiant object that can be freely situated in the observation area of the camera while its image is directly viewed by the camera together with that of the radiant area of interest. We refer to this tool as a "bright pointer". The most usual type is a Cobalt 57 pen marker, although a syringe with Technetium-99m is sometimes used. The localisation method using a bright pointer presents the disadvantage that it leaves a static trail behind as the pointer passes over an area of the image. The image is also greatly affected, as the pointer leaves trails at all the points where it has been.

Localisation and/or navigation systems where radiation is directly involved in the mode of operation will herein be referred to as "radioactive pointers", whether they emit or inhibit radiation. This makes it possible create a particular point on the scintigraphic image that corresponds to the point indicated by a tool used as a pointer.

The cobalt-57 pointer described above as a "bright pointer" belongs to this type of radioactive pointers, but it is not the only one. In the present invention we will show two new types and an improvement in the use of the known bright pointer.

A pointer that inhibits the formation of the image that would normally form in its absence as it passes over the observation area, creating a shadow on the image, will be defined as an "opaque pointer". Likewise, a pointer that does not affect the normal formation of the image due to its presence or absence, but which allows the detection system to know the position of the pointer in relation to the scintigraphic image that is being formed at a particular instant, will be defined as a "transparent pointer".

The methods disclosed in one of the IFIC research group's earlier patents of invention (J. M. Benlloch, F. Sánchez, et al. "Functional Navigator", P200202220 and PCT ES 03-00497), based on an infrared or radiofrequency localiser, is of the transparent type, although it differs completely in that it requires (and this is a disadvantage) two detection systems, which are furthermore based on different technologies. In this case, we will present a localisation method using a transparent pointer that uses the same detection technology (gamma radiation) and the same detector, both for capturing the image of interest and for establishing the spatial location of the pointer. The new invention presented herein has further added value in that it offers the possibility of obtaining information about physical variables regarding the source of interest in the physical position marked by the transparent pointer.

Likewise, US 2004/0075058, invented by I. Blevis, L. Tsukerman and Y. Hefetz, relates to the localisation system of a gamma camera using radio emitters. U.S. Pat. No. 6,723, 988, invented by N. Wainer and Zichron-Yaakov, also relates to the use of mini gamma cameras for navigation equipment.

A mini gamma camera for intra-surgical use must be a light, portable, stand-alone device with one or no cables and it must be capable of forming images in real time.

There are many widely known systems with laser-based pointers. These can generate points, lines and a large range of geometrical forms.

In all known cases where a singular light form is generated on a certain surface due to the intersection of emitted laser light with this surface, said light form is characterised in that its position and shape depend on the distance of the surface intercepted by the light from the laser emitter or emitters, and also on the angular position of the surface; otherwise, the laser emitter or emitters must be symmetrically positioned in relation to the axis on which the laser emitters move towards or away from the surface where their light is intercepted.

Figure 1A:
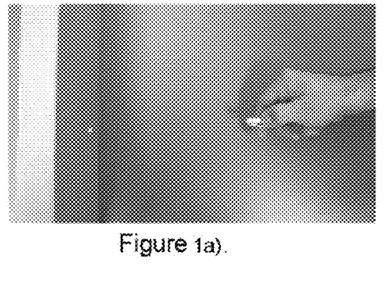
FIGS. 1a) and 1 b) differ in terms of the distance of the emitter and the screen, as the emitter was moved following the same line of emission. As a result, the position of the point of light on the screen at the left does not move.
Figure 1B:
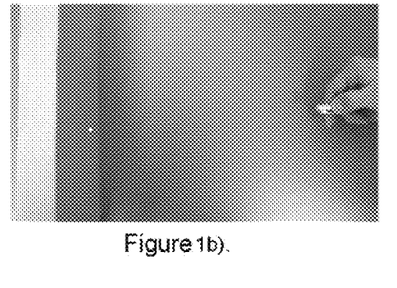

An example of this could be a laser point emitter that moves towards or away from a surface where it generates a point, the axis of movement following the same line as its light. This is a case where the figure generated maintains its position on the surface and its point form, but which is symmetrically situated relative to the axis of movement, and also on said axis, FIGS. 1a and 1b.

Figure 2A:
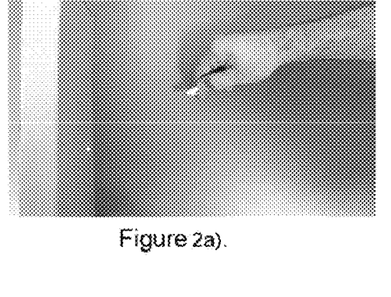
FIGS. 2a) and 2b) differ in terms of the distance of the emitter and the screen, as the emitter was moved following the horizontal axis. As a result, the point of light on the screen at the left of FIG. 2a is vertically higher up than the point of light in FIG. 2b.
Figure 2B:
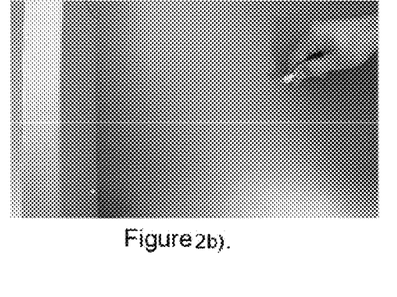

There are many cases of examples where the position or form changes as the position between surface and emitter is moved:
1. A laser point emitter like the one mentioned above, but which moves towards or away from a surface where it generates a point, the axis of movement following a line that forms a certain angle other than zero with the line followed by its light. This is a case where the figure generated is still a point, but its position on the surface changes with the distance between emitter and surface, FIGS. 2a and 2b.
2. A laser emitter with a single transducer, which generates any figure other than a point, generates a figure of a dimension that varies with the distance between emitter and surface and generally also varies with the angle at which this surface is situated relative to the emitter.

DESCRIPTION OF THE INVENTION

Brief Description

The object of the present invention is a novel portable mini gamma camera for intra-surgical use and a localisation system for gamma-ray-emitting objects.

Figure 3:
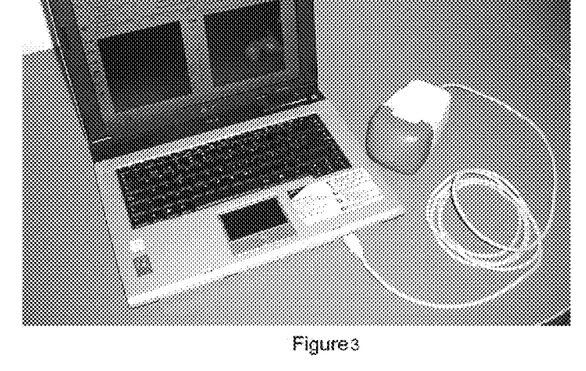
FIG. 3: Light, compact, stand-alone mini gamma camera that can be connected to any computer by a standard communications port. The device shown here is sufficient to perform scintigraphy without requiring any additional system.

The mini gamma camera is based on scintillation crystals and is essentially characterised in that it is a stand-alone device, i.e. all the necessary systems have been integrated together with the sensor head, forming a compact, stand-alone piece of equipment, without the need for any other electronic system, and which can be connected to any standard computer or compatible device by any full-speed or high-speed universal serial interface, Wireless USB, Bluetooth or FireWire, FIG. 3. At the same time, this equipment meets medical grade specifications regarding electrical safety and electromagnetic compatibility.

This invention also presents a special treatment for the surfaces of the crystal, if the scintillation crystal of the mini gamma camera is of the continuous type, and a method that makes it possible to use almost the entire area thereof without the serious disadvantage of image compression and edge effects that occur with the use of continuous crystals. It also introduces the innovation of using rare-earth-based scintillation crystals.

Any gamma ray detector based on continuous scintillation crystals can also be provided with a system for focusing the scintillation light emitted by the gamma ray in order to improve spatial resolution, as the width of light distribution that reaches the photodetector is reduced.

Other innovative characteristics of the mini gamma camera that is the object of our invention are that it can be self-powered from the port of the computer, can save energy, enables software and firmware to be updated from the Internet without the need to interfere with the camera, and can form Real Time Gamma-ray Video (RTGV) images, even at doses administered for low activity, thanks to a new "probabilistic reconstruction" algorithm.

One of the problems presented by gamma cameras is locating objects that appear in the images that they capture in the patient's body, i.e. the correspondence between image and organism. In the present invention, this problem is solved by developing a method of localisation that uses one or more radioactive pointers, using the same gamma camera both to capture the image of interest and to establish the spatial location of each pointer. The new invention presented herein has further added value in that it offers the possibility of obtaining information about physical variables regarding the source of interest in the physical position marked by the transparent pointer. It also introduces a new laser-based light pointer system, which makes it possible to indicate a specific point of the scintigraphic image on the observation area.

The mini gamma camera and localisation systems that have been developed constitute a new surgical navigation system using real time imaging.

DETAILED DESCRIPTION

A mini gamma camera based on scintillation crystal technology and essentially characterised in that it is a stand-alone device, i.e. all the necessary physical and electronic systems have been integrated together with the sensor head, forming a compact piece of stand-alone equipment without the need for any other additional electronic system, and which can be connected to any standard computer or compatible device using a hot-swappable interface.

Figure 4:
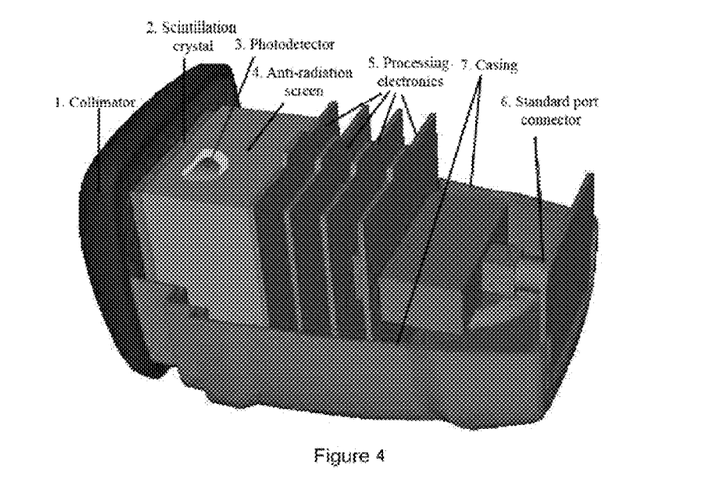
FIG. 4: Isometric diagram of the mini gamma camera.

The structural elements of the mini gamma camera are as follows, FIG. 4:
1. Interchangeable gamma-ray collimation system based on tungsten, lead or another material of the same anti-radiation characteristics.
2. Scintillation crystal.
3. Position sensitive photodetector (or photodetectors).
4. Anti-radiation screen made from lead, tungsten another material of the same anti-radiation characteristics.
5. Low-consumption electronics with analogical or digital processing and power supplies and standard computer connection interface.
6. Interface output connector.
7. Casing with electromagnetic screen.

The collimator 1, with one hole (single pinhole type) or several holes (multiple pinhole type or parallel-hole, converging or diverging type collimator) or a coded mask structure, allows the gamma rays to pass only through the holes established for the correct formation of the image.

The scintillation crystal 2 transduces the energy from a gamma ray, generating a large number of visible light photons, which can be detected by the photodetector 3.

The photodetector 3 receives the light from the scintillation crystal and transduces it into electrical impulses that are sent to the electronic processing section. The photodetector uses a high-voltage power supply of up to 1200V, which is generated on a source plate that forms part of the internal electronic section of the detector head.

The anti-radiation screen 4, made from lead or another material of similar anti-radiation characteristics, covers the side, rear and front surfaces of the camera, except in the area of the collimator 1. Thus, the gamma rays cannot reach the sensitive area of the camera, except through the hole provided expressly for this purpose in the collimator 1, in the case of a single pinhole collimator, or the many holes in the case of multiple pinhole, parallel-hole, diverging, converging or coded mask collimators.

The processing electronics 5 receive the output signals from the photodetector 3. This processing system consists of the following parts:
1. Inter-anode network that reduces to a minimum the number of electronic signals from the anodes of the photodetector for the localisation of the centroid of the light distribution from all the individual anode signals.
2. Analogical signal processing system to amplify, filter and obtain a suitable amplitude according to the charge of each signal.
3. Digital processing system to digitalise the analogical signals, perform digital filtering and send the results to the computer via the established communication interface. It also controls all the device's functions.
4. Power supply system for generating the different voltages required by the equipment from a single 5V supply.

The connector 6 is the equipment's only essential means of communication. Said connector sends data in both direction and in the case of interfaces connected by cable it also supplies power from the computer to the mini camera.

The casing 7 ensures that no light enters the device and reaches the scintillation crystal 2, thus preventing noise from affecting the scintigraphic image to be obtained. The casing also acts as an electromagnetic screen against all kinds of external noise and internal emissions, thereby ensuring a suitable medical grade electromagnetic compatibility.

As all the necessary electronic, analogical, digital, firmware and power supply systems have been integrated into the sensor head, it is possible to achieve a compact mini gamma camera that is exceptionally self-contained and portable. The digital information that the device transmits to the computer means that the scintigraphic image can be directly obtained. For the continuous wireless operation of the camera and the computer, it will be necessary to use an external 5V power supply connected the mains. It can also operate by battery power with the use of wireless interfaces, which frees it of any kind of cable connection.

No other known gamma camera operates as a stand-alone device. However, this feature is very important for intra-surgical use, as it reduces the number of cables to the minimum (one or none, depending on the interface used), and any cable in the operating theatre is a significant obstacle for the surgeon.

A specific object of the present invention is a mini gamma camera of the foregoing characteristics, which meets the medical grade electrical safety and electromagnetic compatibility specifications.

The invention, unlike previous publications by the research group formed by the inventors thereof (see e.g. Nucl. Instr. & Meth. A486 (2002)186-190, Med. Phys. 31, 6 (2004) 1384-1397, Nucl. Instr. & Meth. A525 (2004)298-302, Nucl. Instr. & Meth. A527 (2004)92-96), uses a casing that has been especially designed to meet medical grade electrical safety regulations in a surgical environment. Furthermore, the electronic circuits have been created to operate in an environment without the protection offered by a thick layer of aluminum, as described in said publications.

A specific object of the present invention is a mini gamma camera of the foregoing characteristics, which is also characterized in that the hot-swapped interface can be at least one of the following: a) Full-speed (12 Mb/s) or high-speed (480 Mb/s) universal serial interface (i.e., USB 1.1 or 2.0, respectively); b) Wireless USB; c) Bluetooth (i.e., IEEE Standard 802.15); d) FireWire (i.e., IEEE Standard 1394).

As part of the present invention a USB communications interface has been developed that is up to 400 times faster than that of the academic prototypes mentioned in the prior art. Said interface can communicate using USB 1.1 (12 Mb/s) and USB 2.0 (480 Mb/s), which means that data acquisition speed limitations will be physical for a long time to come. It also prepares this system to operate with new, very high sensitivity collimator systems that are being developed. Communication interfaces using other modern communications ports such as Wireless USB, Bluetooth and FireWire have also been developed, which have not been reported in any other scintigraphy equipment and which provide great versatility in terms of interconnection with standard calculation systems, also making them more portable and easier to use. These advances have also led to a system that can be connected and disconnected from the computer without having to switch it off or take any extra measure.

A specific object of the present invention is a mini gamma camera such as the one described above, with the characteristic of being self-powered, as it can use the standard external data interface of the computer as a power supply, or alternatively a battery, not requiring the use of mains electricity or any other external power supply.

This is possible thanks to the fact that the mini gamma camera that is the object of the present invention consumes less power than the power outputs offered by the ports that are used. The equipment may also have an external power supply (which will not be essential) using a direct 5V 500 mA supply.

A specific object of the present invention is a mini gamma camera such as the one described above, with the characteristic that it can go into energy-saving modes, as the software can define several levels of power consumption according to the functional requirements at each moment.

As part of the power supply control, the mini camera can go into "sleep" mode, in which it consumes just 2 microamperes, without losing the ability to "wake up" and change to another state if the software gives an automatic order to do so. The next energy state consumes 23 mA and allows two-directional data communication between the camera and the computer, with functions such as identification and pre-establishment of data acquisition conditions. At another level that consumes 320 mA, the device can generate background noise level acquisition, carry out functionality checks and adjust its systems to counteract noise. At another level that consumes 150 mA, the system can maintain the optimum temperature of the sensor system so that it can start an acquisition quickly.

Finally, with a consumption of 470 mA and all the systems switched on, the equipment can carry out any operation, according to its purpose.

By making appropriate use of these features, the equipment does not have to be unplugged from the computer, saving energy whilst also lengthening the useful life of the equipment. No mechanical buttons are needed to switch the equipment off.

A specific object of the present invention is a mini gamma camera such as the one described above, wherein the software can be updated from the Internet and firmware (hardware controller) can be recharged from the software without having to open the camera, which means that it is possible to alter the hardware and/or add other features to it by means of firmware updates.

This exclusive characteristic makes it possible for the manufacturer to include new advances and improvements to mini cameras marketed anywhere in the world by providing a downloadable update, which registered clients would have access to.

It is usual for certain modern consumer electronic devices that operate using software to be updated in this way. It is less usual for it to be possible to update the firmware that controls the hardware without having to open up the equipment that contains that hardware. There is no known gamma camera in which this characteristic is implemented.

The operation of the digital system of the mini gamma camera that is the object of the present invention is based on a microcontroller and it presents a hardware design with a set of facilities that are additional to those required for scintigraphic imaging. The use of these extra features has not yet been developed in the current scintigraphy software, and they are not included in the program that operates in the microcontroller (firmware). What we claim is that our equipment will be able to use these features once they are developed. This may be done by simply sending the corresponding update by a computerised means and the currently created system will be able to update both the computer software and the firmware of the microcontroller of the mini gamma camera.

These hardware updates are, of course, limited to the features created and not used in the original hardware design. However, the scintigraphic imaging firmware that is currently used may be upgraded as many times as necessary and practically unlimitedly, based on the same starting data and perhaps some characteristic of the unused features.

For example, computer updates could be used to add to the system the possibility of converting it any of the following pieces of equipment, apart from a gamma camera:
1. Radiation level detector.
2. Multi-channel spectrometer.
3. Single-channel spectrometer with a moveable window.
4. Thyroid count capturing system.

A specific object of the present invention is a mini gamma camera of the aforementioned characteristics, with the additional characteristic that the scintillation crystal is of the continuous type, which has undergone a special treatment of its outer surfaces, and a specific algorithm called "compensated affine transformation" has been used to make it possible to achieve inhomogeneity in the detection area of less than 5% in up to about 80% of said area, overcoming the old limitations known as edge effects that limit the useful area to 50% of the sensitive area.

Although some patents (see ES 2202846, invented by A. Soluri and R. Pani; ES 2206924, invented by A. Soluri) give a minor mention to the possibility of using continuous crystals in mini gamma cameras, said patents are based, according to all their examples of embodiment, on pixelated crystals.

However, none of said patents explain how to overcome the serious edge and compression problems affecting the image that occur when the detection surface is small in relation to the width of the crystal, in the direction in which the gamma rays enter as is the case, by definition, with mini gamma cameras. Said problems have an insignificant effect in the case of the large gamma cameras that have traditionally been used, and therefore the authors of said patents overlook such problems. However, as is shown in the publications by the research group formed by the authors of the present invention (Nucl. Instr. and Meth. A486 (2002)186-190, Med. Phys. 31, 6 (2004) 1384-1397, Nucl. Instr. and Meth. A525 (2004)298-302, Nucl. Instr. and Meth. A527 (2004)92-96) said problems are important and substantially reduce the useful field of detection of the cameras if, as required by the regulations (Performance Measurements of Scintillation Cameras, NEMA Standards Publication no. NU 1, National Electrical Manufacturers Association, Washington D.C. 1994), the detection surface is to be uniform. Therefore, although the use of continuous crystals is cited in some patents, no method has yet been invented for their practical use in small field of view cameras without them generating edge effects and a lack of uniformity that exceed those permitted by the regulations, e.g. the aforementioned NEMA standards. For this reason they are not used in practice.

The present invention introduces a special treatment for the surfaces of the crystal and an algorithm that make it possible to achieve relatively large useful fields of view (using almost the entire area of the crystal), which cannot be achieved by current continuous crystal systems, which is the main reason why this technique is not currently used in mini gamma cameras outside academic circles.

Furthermore, the use of continuous crystals with a suitable surface treatment makes it possible to achieve a greater amount of light in the photosensitive device than crystals in the form of a pixel array, which results in an improved energy resolution of the gamma ray detector.

The surface treatment that is applied to minimise the edge effects will be described below. The surface via which the gamma rays penetrate into the crystal has been roughly polished, painted with a dry, reflective white paint and coated with a reflective white epoxy layer thereon. Alternatively, this surface can be finely polished and coated with a self-reflective layer. The self-reflective layer has the property that the particles of light emitted by the crystal, which fall on said layer, are reflected at the same angle as the emitted light that falls on the crystal, but in the other direction. The surface of the crystal that is in contact with the photodetector is also roughly polished. Finally, the small side surfaces are roughly polished, painted with dry, absorbent black paint and also coated with an absorbent black epoxy layer. The difference between this treatment and the one described in the previous publications by the research group to which the authors of the invention belong (see e.g. "PORTABLE MINI GAMMA-CAMERA FOR MEDICAL APPLICATIONS", by E. Porras, B. Escat, J. M. Benlloch, D. Kadi-Hanifi, S. López, N. Pavón, J. A. Ruiz, F. Sánchez, A. Sebastiá, Nuclear Instruments & Methods in Physics Research A 486, 2002, 186-190; "DESIGN AND TESTS OF A PORTABLE MINI GAMMA CAMERA", by F. Sánchez, J. M. Benlloch, B. Escat, N. Pavón, E. Porras, D. Kadi-Hanifi, J. A. Ruiz, F. J. Mora, A. Sebastiá, Medical Physics 31, 6, June 2004, 1384-1397) is considerable in terms of reducing edge effects and improving uniformity.

In the article by D. P. Mc Elroy, S. C. Huang and E. J. Hoffman, "The Use of Retro-Reflective Tape for Improving Spatial Resolution of Scintillation Detectors" (IEEE Trans. Nucl. Sci. Vol 49 (1) (2002) 165-171) retro-reflective strips are used to improve the intrinsic spatial resolution properties of a continuous crystal in gamma cameras. However, the use of a retro-reflective layer has never been implemented in mini gamma cameras.

Despite said optimum treatment of the surface of the crystal, it is necessary to apply a specific algorithm, which we call "compensated affine transformation", to minimise image compression and edge effects to achieve a uniform detection surface of the maximum possible size.

The algorithm first breaks down the surface of the detected (compressed) image into polygons (e.g. triangles) with a small area and an affine transformation is carried out so that each polygon is expanded, maintaining its shape. The expansion factor depends, among other factors, on the specific characteristics of the crystal and photodetector that are used and on the situation of the polygon in relation to the centre of the detection surface, it generally being greater for polygons situated on the limits thereof than in the centre. A lookup table (LUT) is used to make quick and efficient local corrections of position and energy. Moreover, the gamma rays that have been detected in a given polygon are redistributed into expanded polygons using a Monte Cario method that takes into account the probability that the detected gamma ray had actually fallen within another adjacent polygon. The uniformity is therefore optimised in the largest possible detection area.

In the previous publications by the research group formed by the authors of the present invention (see e.g. "A FLAT-PANEL-BASED MINI GAMMA CAMERA FOR LYMPH NODES STUDIES", by M. M. Fernández, J. M. Benlloch, J. Cerda, B. Escat, E. N. Giménez, M. Giménez, Ch. W. Lerche, J. Martínez, N. Pavón, F. Sánchez, A. Sebastiá, Nuclear Instruments & Methods in Physics Research A 527, 2004, 92-96) a decompression method is used on the detected image, which is based on functions of two variables with monomial multiples. The fundamental problem with said method is that it cannot be used in real time due to its slowness because of the large number of algebraic operations that it involves. It also lacks the possibility of being optimally adapted to the local characteristics of the detection surface, which can vary considerably, e.g. according to the illuminated anode pads (if the detector is a position sensitive flat panel photo-multiplier).

Figure 5:
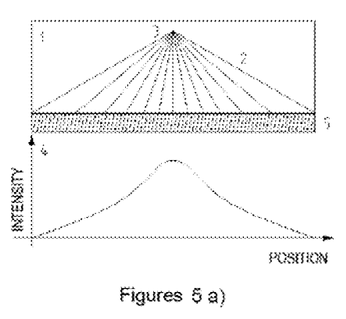
Figure 6A:
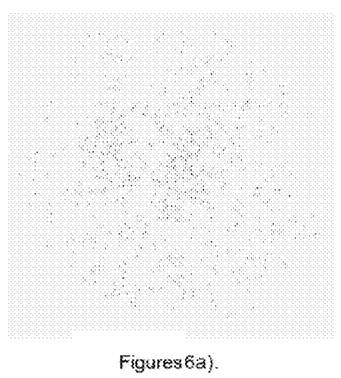
FIG. 6a) Planar image generated in thyroid scintigraphy according to the standard method with 600 events.
Figure 6B:
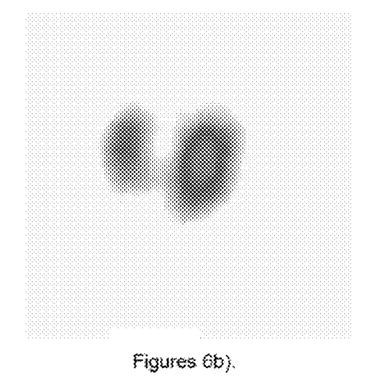
FIG. 6b) Image generated by automatic reconstruction using the same 600 events as in FIG. 6a).
Figure 6C:
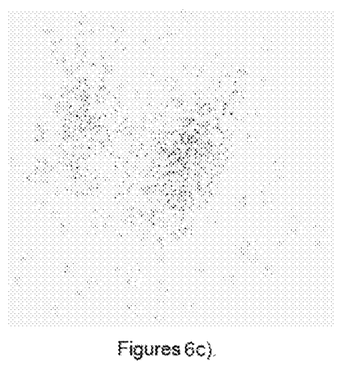
FIG. 6c) Planar image generated in thyroid scintigraphy according to the standard method with 3000 events.
Figure 6D:
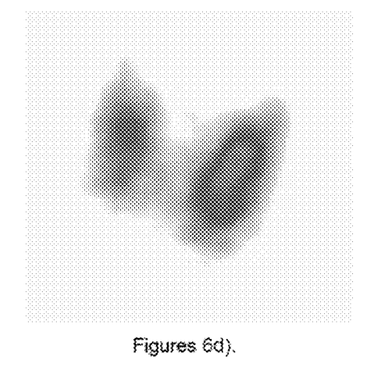
FIG. 6d) Image generated by automatic reconstruction using the same 3000 events as in FIG. 6c).

An additional object of the present invention is a gamma ray detector based on continuous scintillation crystals improved by a system for focusing the scintillation light emitted by the gamma ray, thus reducing the width of light distribution that reaches the photodetector, FIGS. 5a and 5b.

The spatial resolution of a gamma ray detector based on continuous scintillation crystals depends of the width of light distribution emitted by the gamma ray onto the crystal and which reaches the surface of the photodetector: the greater the width of distribution, the more difficult it is to separate two points from each other and therefore the lower the resolution. Moreover, the greater the width of light distribution, the greater the edge effects that occur with the use of continuous scintillation crystals, increasing the compression factor of the image.

Said improvement that is introduced in the present invention is therefore particularly important in the case of gamma ray detectors with thick scintillation crystals, in the direction perpendicular to the surface of the photodetector, in relation to said surface. Said detectors present the difficulty that most of the interactions occur close to the surface where the gamma rays enter the crystal and they therefore generate very wide light distributions on the surface of the photodetector.

Said system for focusing the scintillation light emitted by the gamma ray can be implemented by adding one or more layers of optical material that act as lenses thereto. In particular, the use of layers of converging lenses or micro-lenses with a similar focal distance to the dimension of the crystal in the direction perpendicular to the surface of the photodetector reduces the width of light distribution that reaches it. To achieve a greater reduction in the width of light distribution, the continuous crystal can be segmented into two or more layers along the direction perpendicular to the photodetection surface, adding a layer of converging micro-lenses between every two of said layers.

A specific object of the present invention, which is a consequence of the above, is a gamma ray detector that consists of several layers (in the direction in which the gamma rays enter) of continuous scintillation crystals, and finally photodetectors, and in which a layer of converging lenses or micro-lenses has been added between every two of said layers.

The invention is useful in any gamma ray detection system based on scintillation crystals, e.g. in positron emission tomography (PET) cameras, single-photon emission computed tomography (SPECT) and gamma cameras in general.

A specific object of the present invention is the use of a gamma ray detector according to claims 8 or 9 in a mini gamma camera such as that of claim 1, or in a PET or SPECT camera, or a gamma camera based on scintillation crystals in general.

A specific object of the present invention is a mini gamma camera such as the one described above, with the characteristic that the main component of the scintillation crystal is a chemical element belonging to the rare earth type, such as $LnBr_3$ or $LnCl_3$.

Crystals of the type in which the main component is a chemical element belonging to the rare earth type considerably improve the functionality of the mini camera. This is because said scintillation crystals make it possible to achieve an energy resolution of the detected gamma rays that is comparable to that of detectors based on semiconductor technology. This characteristic is critical in order to distinguish between different radioactive isotopes, as it is possible to separate the corresponding energies. This ability to separate the energies enables us not only to reduce the background noise, as the size of the energy window is reduced, but also to apply the localisation method described below more efficiently.

Furthermore, crystals of the type in which the main component is a chemical element belonging to the rare earth type produce a larger amount of scintillation light, with the consequent increase in photon detection statistics, which improves the spatial resolution of the gamma camera. At present, these crystals cannot be grown to a very large size, which means that they can only be used in small gamma cameras. Moreover, a manufacturing method has not yet been developed to produce pixel arrays from said crystals. Their use in the mini gamma camera with continuous crystals in which the edge problems have been solved therefore represents an optimum application thereof.

A specific object of the present invention is a mini gamma camera such as the one described above, with the characteristic that the photodetector is of the position sensitive flat panel photomultiplier type.

One of the essential properties of said type of photomultiplier is that its design has been considerably improved to avoid dead areas at the edges of the device, thus facilitating the modular connection of several flat panel photomultipliers. Furthermore, it hardly presents edge effects, which makes it particularly suitable for use in mini gamma cameras and even more so when continuous crystals are used, as is the case with the present invention. Some patents (ES 2202846, invented by A. Soluri and R. Pañi; ES 2206924, invented by A. Soluri; WO 00/19238, invented by S. Majewski, A. Weisenberger, and R. Wojcik) disclose the use of position sensitive photomultipliers, of the type that use crossed wire anodes. Flat panel photomultipliers have multi-pad anodes, rather than wire anodes. ES 2206924, invented by A. Soluri, mentions the possibility of using any type of position sensitive photomultiplier; however, flat panel photomultipliers did not appear until 2002, which means that they could not be the object of said patent (which is from 1998).

An additional object of the present invention is a scintigraphic image creating algorithm called "probabilistic reconstruction", which is based on assigning each detected gamma ray of a distribution the probability that the emission point has occurred at each point of the possible radiation emission region, taking into account the point of impact detected by the detection system, the intrinsic resolution of the detector system, the uniformity of the detector, the geometry thereof and the geometry of the optical system that is used.

The assignation mainly consists of attributing a probability to the direction of linear impact according to the value of uniformity at said point and attributing a probability to its vicinity, taking into account this and the other aforementioned variables.

Different filters are currently used to soften the image, the purpose of which is to minimise the effect of a lack of sufficient statistics in certain regions. Said filters are only applied once the final image has already been obtained. Using the "probabilistic reconstruction" algorithm claimed herein, said softening is automatically performed in real time, event by event, thus accelerating the formation of the final image, FIGS. 6a, 6b, 6c and 6d.

"Probabilistic reconstruction" is a development that makes it possible to achieve still gamma ray emission images of a quality that is comparable to that achieved using conventional methods, but using a considerably lower number of detected gamma rays. This development therefore makes it possible to achieve images in a much shorter time. In practice, with the doses of radiopharmaceuticals that are currently administered, this means that images can be achieved in real time. Alternatively, it could mean a reduction in the dose that is administered to achieve an image of the same quality.

Therefore, a specific object of the present invention is the use of the aforementioned "probabilistic reconstruction" algorithm, and a gamma camera, such as the one described above, but not limited thereto, for the formation of an image in real time of a quality that is comparable to that achieved using conventional methods, but using a considerably lower number of detected gamma rays.

"Probabilistic reconstruction" is a development that makes it possible not only to achieve still gamma ray emission images of a quality that is comparable to that achieved using conventional methods, using a considerably lower number of detected gamma rays, but also to form Real Time Gamma-ray Video (RTGV) images from radiant objects, even low-activity objects, as the camera moves over the observation area. This does not require an increase in the usual dose to be injected into the patient, as the mini gamma camera uses the same information as any conventional camera would receive. The difference lies in the way the information is processed and the ease with which this portable camera can be moved.

Therefore, a specific object of the present invention is the use of the aforementioned "probabilistic reconstruction" algorithm, and a gamma camera, such as the mini camera gamma described above, but not limited thereto, to achieve Real Time Gamma-ray Video (RTGV) images from radiant objects, even low-activity objects, as the camera moves over the observation area.

An additional object of the present invention is a device based on at least two mini gamma cameras of the aforementioned characteristics, which are mechanically correlated and operated simultaneously by the same control system, in order to achieve stereoscopic vision, thereby making it possible to view gamma ray emitting objects in three dimensions. This is not a technique of single or dual photon emission tomography or stereoscopic vision by triangulation (as is mentioned in PCT/ES03/00497 "Functional Navigator", the main authors of which are also the inventors of the present invention), but rather a true stereoscopic vision based on images taken by two sensors with only slightly different visual perspectives that are processed by a system capable of recognising and comparing image patterns. The use of this device would be mainly for intra-operative use in the three-dimensional localisation of deep malignant regions.

One possibility for localisation other than that disclosed in the prior art is what we call "transparent pointer" localisation, wherein the image of the radiant object of interest is not affected by the presence of the pointer or localisation system.

An additional object of the present invention is a "new method of localisation and measurement" of physical variables of radiation-emitting objects based on the use of two elements, which are listed below:

1. At least one "transparent pointer" (i.e. that emits radiation that can be distinguished from the radiation that is to be observed).
2. A gamma ray detection system (including but not limited to that of the object of the present invention), which is capable of simultaneously detecting the pointer and said sources of interest, FIGS. 7a and 7b. The method consists of the (three-dimensional) automatic spatial localisation of the pointer by the gamma camera (without necessarily presenting the scintigraphic image of the pointer) and the acquisition and displaying of the image from the source of interest. The apparent physical variables, e.g. apparent activity, can be determined in the portion of the region of interest that is indicated by the pointer. On the basis of said values of the physical variables and the data obtained from the pointer, it is possible to determine the absolute values thereof in the indicated part of the region of interest.

The pointer can be a known source of activity, in which case the position thereof is determined in the three-dimensional space. This is because not only the point of impact on the detection plane of the mini gamma camera is detected, but also the distance in relation to said point is estimated on the basis of the apparent activity thereof, as its absolute activity is known. It is also possible to determine the distance of the pointer in relation to the camera, based on the known dimensions of the pointer and the collimator and by measuring the apparent size of the image formed by the pointer.

One way of distinguishing the pointer from the rest of the radioactive area is by energy filtering, provided that the energy emitted by the pointer is sufficiently distant from energy of the radiopharmaceutical that is used.

An additional object of the present invention is an "improved method of localisation" for radiation-emitting objects based on the use of three elements, which are listed below:
1. At least one "bright pointer" (radiation that cannot be distinguished from the radiation that is to be observed).
2. A gamma ray detection system (including but not limited to the camera that is the object of the present invention), which is capable of simultaneously detecting the pointer and said sources of interest, although not of distinguishing between them.
3. A sufficiently fast mechanism of generating images with limited persistence.

The method consists of using a mode of acquisition with limited persistence so that the pointer can be moved over the camera's observation area without leaving a (bright) trail behind it, except in its current position, thus reducing the effect that the traditional method has on the image that is captured.

For this to be valid in practice, it is essential to use a high-sensitivity camera or otherwise a camera that can achieve images quickly enough, such as the one described herein. The formation of Real Time Gamma-ray Video (RTGV) images, according to the "probabilistic reconstruction algorithm", makes it possible to use these bright pointers to locate different radiation-emitting points by situating the bright pointer close to the source that is to be located.

Another variant that can be applied using this type of pointer is that of acquiring a still image for the time needed for it to form correctly, after which the system goes into a special acquisition mode in which it waits until only the bright pointer appears as an extra object in the image data. The equipment can internally subtract the new image data from the original image data at each moment, so that only those corresponding to the pointer remain. These data make it possible to establish and show the exact position of the pointer in relation to the original scintigraphic image, which will still be shown at all times without being altered by the pointer.

Having explained the use of anti-radiation screens to virtually delete a bright object from the scintigraphic image, as was described in the prior art section, and the use of a cobalt-57 pointer (bright pointer) that acts as a localiser, as was described above, we now come back to the concept of "opaque pointer" as an object that is capable of stopping radiation from passing and which can be freely situated in the camera's observation area as the image of the radiant object of interest is viewed. The image that will be seen without the opaque pointer differs from that obtained with the pointer, as the rays cannot pass therethrough. With a tool like this it is possible not only to cover up a high-activity region in order to improve the visualisation of the rest of the image, as was explained above, but also, independently, to see the spatial situation of observable regions of the scintigraphic image thanks to the "shadow" created on the image by the "opaque pointer". It is unknown for a "material that is opaque to gamma rays" to be used expressly as a localiser for radiation-emitting points or regions on a scintigraphic image.

An additional object of the present invention is a "new method of localisation" for radiation-emitting objects based on the use of the elements listed below:
1. At least one "opaque pointer" (it does not radiate or allow the radiation that is to be observed to pass therethough);
2. A gamma ray detection system (including but not limited to that of the object of the present invention), which is capable of detecting the radiant sources of interest;
3. A sufficiently fast mechanism of generating images with limited persistence, such as that used to generate Real Time Gamma-ray Video images, but not limited thereto.

Figure 8A:
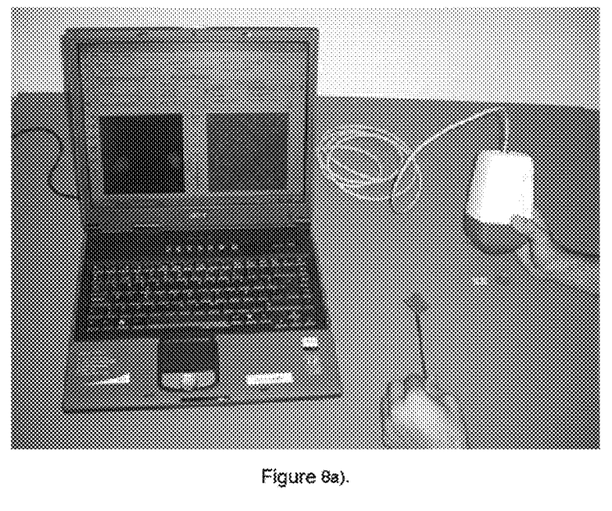
FIG. 8a) The camera is held in the right hand. The system is adjusted to achieve real time video images (limited persistence) of two sources of emission. The "opaque pointer" is held in the left hand but is not yet used. The computer displays the image acquired in the acquisition window of the software situated on the left of its screen.
Figure 8B:
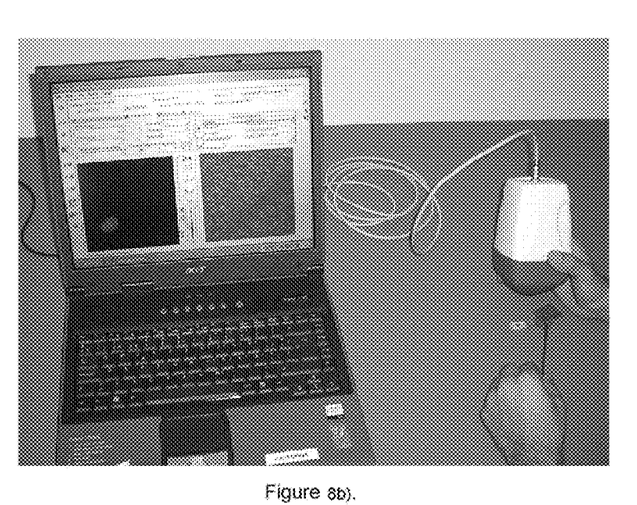
FIG. 8b) Using the same system settings as in FIG. 8a), the "opaque pointer" is now placed between the right-hand source and the camera, preventing its image from forming, as can be seen in the computer's acquisition window.
Figure 8C:
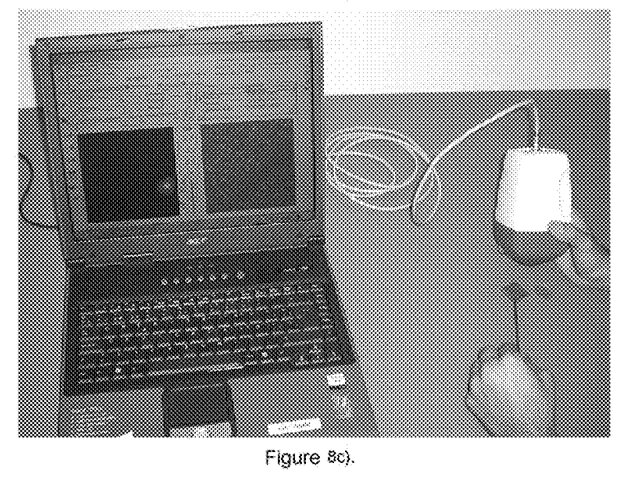
FIG. 8c) Using the same system settings as in FIG. 8a), the "opaque pointer" is now placed between the left-hand source and the camera, preventing its image from forming, as can be seen in the computer's acquisition window.

The method consists of using a mode of acquisition with limited persistence, FIGS. 8a, 8b and 8c, so that the pointer can be moved over the camera's observation area without leaving a (shadow) trail behind it, except in its current position, thus limiting the shadow that affects the image that is captured at the moment it is observed.

For this to be valid in practice, it is essential to use a high-sensitivity camera or otherwise a camera that can achieve images quickly enough, such as the one described herein. The formation of Real Time Gamma-ray Video (RTGV) images, according to the "probabilistic reconstruction algorithm", makes it possible to use these opaque pointers to locate different radiation-emitting points by making the image disappear when the opaque pointer is situated between the source that is to be located and the camera.

As with the bright pointer, the opaque pointer can be used in a special mode to establish its position on the basis of the difference in the images before and after it is put into action. The principle is the same, except that in this case the sign of the image resulting from the subtraction is negative; however, in both cases the modular value of the counts that are acquired (which is positive) enables us to find out current position of the opaque pointer.

Opaque, bright and/or transparent pointers can be used with different gamma-ray-based systems, such as gamma cameras, mini gamma cameras, SPECT gamma cameras and PET cameras for locating lymph nodes, tumours and organs in human beings and animals, and for measuring the physical variables associated with them.

Opposite to how radioactive pointers work, it is possible to create a particular point in the body being observed, which corresponds to an established position on the scintigraphy image being observed (e.g. the centre of the image). In this case, we have invented a new system based on laser pointers that achieve this purpose in a different way to any known laser pointer system.

An additional object of the present invention is a device that makes it possible, through the use of light emitters, to generate a singular light form with a fixed position on a surface, even if the distance from the emitters to the surface can vary along an axis that runs from the device to the surface, with the particularity that said axis does not cross the spatial position of the light emitters, but can be aligned or made to coincide with the characteristic planes of emission of the light sources.

A particular case of our invention consists of a system that uses laser emitters situated asymmetrically in relation to the axis of movement between the surface and the emitter system, which is capable of creating a singular light form as it intercepts the surface, with the characteristic that the geometrical form of the light that is generated and its position do not depend on the distance between the emitter system and the illuminated surface, from a certain minimum distance.

Figure 9:
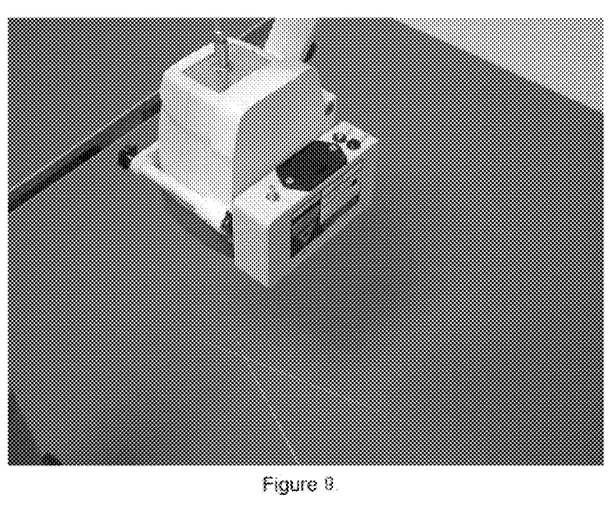
FIG. 9: Photograph of a laser pointer based on that disclosed herein and coupled to a gamma camera such as the one also disclosed herein. It can be seen that the crossing of the laser emissions indicates the centre of the camera's field of view. This characteristic is valid regardless of the distance at which the system is from the surface "observed" by the camera.

One immediate use of this invention is the possibility of marking a singular point that indicates the axis of observation of a device such as a gamma camera (but not limited thereto), without having to situate light emitters on and opposite said axis, which would affect the functionality of the equipment by obstructing the entry of the rays that are going to be detected. These can be situated in positions surrounding said axis and at a considerable distance if necessary. FIG. 9.

The basis of the invention is a geometrical construction that will be described below:

If we take two laser emitters of the type commonly called line emitters, i.e. that generate straight lines on a flat surface. These really generate portions of planes in the three-dimensional space. The intersections of different planes in the space create straight lines in the space. The intersections of portions of planes in the space also generate segments of straight or semi-straight lines in the space. Laser light emitters are ideal for a device like this, but they are not the only type that can work.

If the line emitters mentioned above are situated in such a way that their planes of emission are different, but both of them intercept the axis of movement on which the emitter system and the surface that intercepts the light of both emitters move relatively, then the intersection of the portions of planes of emitted light generate a semi-straight line of light situated exactly on the straight line followed by the aforementioned axis of movement and therefore the light of both emissions will always cross at the same point (in the same position) on the surface that intercepts the light emissions, even if the surface moves on that axis in relation to the emitter system.

If our singular form is the generation of a point where the lines of light cross, then the above-described system is an example of generation of a singular form that maintains its position on a surface, even if it moves in relation to the emitter system following a straight axis, which does not coincide with the position in which the light emitters are situated, and they are not situated symmetrically in relation to the axis of movement. The most simple singular form of generation is a cross (X), but this is not the only form that can be used.

The light pointer system that has just been described has a wide field of applications that goes beyond gamma cameras and which includes other structural and functional image devices.

If in addition to the above, the line emitters are situated in a transversal position that coincides with the focus of a camera of diverging or pinhole collimators, and the angle of light emission of each light emitter is adjusted according to the angle of vision of the device, then the external limits of the crossed light beams can provide information about the device's field of view.

BRIEF DESCRIPTION OF THE DRAWINGS

FIG. 1: A laser pointer (pen) is held in one hand as it lights a specific point on a screen situated to the left of the photograph.

FIG. 2: The same laser pointer as shown in FIG. 1 is held in one hand as it lights a specific point on a screen situated at the left of the photograph, with the particularity that the direction of emission of the laser forms a considerable angle relative to the horizontal axis that joins the emitter and the screen.

FIG. 5 a) Light distribution in continuous crystal without focusing system.

FIG. 5 b) Light distribution in continuous crystal with focusing system.

EXAMPLES

Example 1

Embodiment of a Compact Stand-Alone Mini Gamma Camera with Localisation System for Intra-Surgical Use The mini gamma camera that is shown (FIGS. 3 and 4) consists only of the sensor head, a USB cable and a standard computer. It has an irregular, ergonomic, rectangular prismatic shape with the following dimensions: 70 mm high, 90 mm wide and 140 mm long. It weighs just under 1 kg, including the collimator. The system's small dimensions, ergonomic shape and light weight make this a portable, hand-held device. This mini gamma camera is used to view small organs such as the sentinel lymph node in an intra-operative situation with a positional resolution of less than 2 mm.

This portable mini gamma camera can "see" an energy range from 15 keV to 250 keV, although its design has been optimised for the 50 keV to 200 keV region, in which the most widely used radioactive sources in medical imaging are found (e.g. Tc-99m, which emits 140 KeV gamma rays). This camera has a single position sensitive photomultiplier tube of the multi-anode type coupled to a CsI(Na) scintillation crystal. Different collimators can easily be coupled thereto and it includes a complete electronic system with the high-voltage power supply of the photomultiplier and analogical and digital signal processing, therefore not requiring any card to be inserted into the computer, or any other additional electronic circuit. The equipment can be hot-swapped, i.e. with the computer switched on, and it does not require an additional power supply cable, only the USB cable.

The maximum electricity consumption is 5V 470 mA. It consumes less than 100 mA at start-up, with a gradual start-up system and the possibility of going into low energy modes (23 mA) and suspension (10 μA), for complete compatibility with the USB specification.

FIG. 9 shows how the mini camera that is the object of this invention is connected to a laser localisation system, which is also disclosed herein. It generates an "X" shape in the central position of the mini camera's field of view. This allows the surgeon to locate "hotspots" such as the sentinel lymph nodes, which will be marked with said "X" when the image thereof appears in the centre of the scintigraphic image.

Example 2

Use of a Compact Stand-Alone Mini Gamma Camera with Gamma Navigation System for Intra-Surgical Use FIGS. 7 and 8 show the mini gamma camera that is the object of the present invention being used with radioactive navigation systems.

Figure 7A:
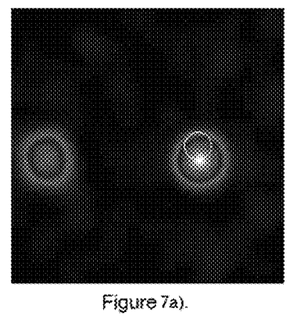
FIG. 7a) Image of two radioactive sources, plus the automatic indication of the position of the transparent pointer above the source situated on the right.
Figure 7B:
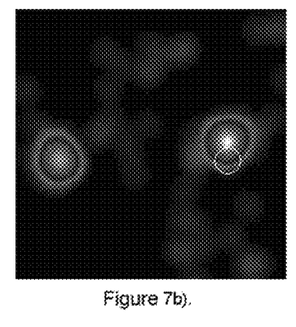
FIG. 7b) Image of two radioactive sources, plus the automatic indication of the position of the transparent pointer below the source situated on the right.

FIGS. 7a and 7b show two images captured by the mini gamma camera, at the moments when a 125I pointer was positioned above and below one of two cobalt sources that were used as sentinel lymph node phantoms.

FIGS. 8a, 8b and 8c show three photos of the mini camera gamma and the computer connected thereto, at the three moments when the opaque pointer (lead screen) was a) absent, b) positioned over the right-hand source and c) positioned over the left-hand source, whilst the computer shows the shadow effect left by said pointer on the scintigraphic image, showing how the method can be used to locate "hotspots" such as sentinel lymph nodes.

The invention claimed is:

1. A system for the diagnosis, navigation, positioning, localization and detection of radioactive sources in radio-guided surgery, comprising:
    a localization system based on radioactive pointers capable of being moved over the radioactive sources to be observed;
    a laser-based light pointer system, to indicate a specific point of the image on an observation area; and
    a mini gamma camera, that captures images of organs and images of at least one radioactive pointer,
wherein the localization system detects the point of impact of the radioactive pointer on a detection plane of the mini gamma camera and the estimated distance from the pointer to the impact point on the camera on the basis of the activity of the radioactive pointer and its apparent activity.

2. The system according to claim 1, further comprising a control system comprising a computer with a specific and updatable scintigraphy software and a connection media between the mini gamma camera and the control system for a specific standard interface, wherein the control system controls the mini gamma camera, sending automatic orders by means of two-directional data communication and receiving acquired data from the mini gamma camera.

3. The system according to claim 2, further comprising a radiation level detector based in a computer software update of the system.

4. The system according to claim 2, comprising a plurality of mini gamma cameras which are mechanically correlated and operated simultaneously by the control system, in order to achieve stereoscopic vision, thereby making it possible to view gamma ray emitting objects in three dimensions.

5. The system according to claim 1, wherein the mini gamma camera is integrated into a sensor head, comprising:
    a casing having an interior space, the casing comprising an electromagnetic screen;
    an interchangeable gamma ray collimation system, disposed within the interior space of the casing, that allows the gamma rays to pass only through holes established for the correct formation of the image;
    a continuous-type scintillation crystal that transduces the energy from a gamma ray generating a large number of visible light photons, which can be detected by a photodetector;
    a hot-swappable computer interface, cooperatively connected to the processing electronics, designed for low-energy consumption; and
    an anti-radiation screen, covering the side, rear and front surfaces of the camera, except in the area of the collimation system;
wherein all of the above-listed elements of the mini gamma camera have been integrated together with the sensor head, forming a compact piece of stand-alone equipment without the need for any other additional electronic system.

6. The system according to claim 5, wherein the hot-swappable interface of the mini gamma camera is selected from the group consisting of USB 1.1, USB 2.0, wireless USB, IEEE 802.15, and IEEE 1394.

7. The system according to claim 5, wherein the mini gamma camera is configured to draw power from a power source selected from the group consisting of the hot-swappable computer interface, and a battery.

8. The system according to claim 5, wherein the mini gamma camera is configurable to enter into an energy-saving mode.

9. The system according to claim 5, wherein the continuous-type scintillation crystal has an inhomogeneity in a detection area of less than about 5% up to about 80% of said area.

10. The system according to claim 9, wherein the surface of the continuous type scintillation crystal of the mini gamma camera via which the gamma rays penetrate is roughly polished, painted with a dry, reflective white paint, and coated with a reflective white epoxy layer thereon.

11. The system according to claim 9, wherein the surface of the continuous-type scintillation crystal of the mini gamma camera through which the gamma rays penetrate is finely polished and coated with a self-reflective layer.

12. The system according to claim 9, wherein the surface of the continuous-type scintillation crystal of the mini gamma camera that is in contact with the photodetector is roughly polished.

13. The system according to claim 9, wherein the small side surfaces of the continuous-type scintillation crystal of the mini gamma camera are roughly polished, painted with dry, absorbent black paint and coated with an absorbent black epoxy layer.

14. The system according to claim 5, wherein the mini gamma camera further comprises a system for focusing the scintillation light emitted by the gamma ray, reducing the width of light distribution that reaches the photodetector.

15. The system according to claim 5, wherein the scintillation crystal of the mini camera comprises a chemical element belonging to the rare earth type.

16. The system according to claim 5, wherein the photodetector of the mini camera comprises a position sensitive flat panel photomultiplier.

17. The system according to claim 1, wherein the mini gamma camera is a SPECT or PET gamma camera.

18. The system according to claim 1, wherein the radioactive pointer is a transparent pointer that emits radiation that can be distinguished from the radiation that is to be observed, a bright pointer that emits radiation that cannot be distinguished from the radiation that is to be observed, or an opaque pointer that does not radiate or allow the radiation that is to be observed to pass.

19. A system for the diagnosis, navigation, positioning, localization and detection of radioactive sources in radio-guided surgery according to claim 1, further comprising a collimator and wherein the localization system determines the distance of the radioactive pointer in relation to the camera, based on the dimensions of the radioactive pointer, the dimensions of the collimator and measuring an apparent size of the image formed by the radioactive pointer.

20. A system for the diagnosis, navigation, positioning, localization and detection of radioactive sources in radio-guided surgery according to claim 1, wherein the laser-based light pointer system comprises laser emitters situated asymmetrically in relation to the axis of movement between the surface and the emitter system in such a way that the geometrical form of the light that is generated and its position does not depend on the distance between the emitter system and the illuminated surface.

21. The system according to claim 1, wherein the radioactive sources are lymph nodes, thyroid, parathyroid, kidneys, colon, breasts and other organs of a patient who has been administered a radioactive dose of a radiopharmaceutical related to the organ and a function to be observed.

* * * * *